US010449537B2

(12) United States Patent
Sharpe et al.

(10) Patent No.: US 10,449,537 B2
(45) Date of Patent: Oct. 22, 2019

(54) CAPILLARY MANIPULATION OF CLINICAL SAMPLES

(71) Applicant: DNA Medicine Institute, Inc., Cambridge, MA (US)

(72) Inventors: Julia Z. Sharpe, Cambridge, MA (US); Eugene Y. Chan, Boston, MA (US)

(73) Assignee: DNA Medicine Institute, Inc., Cambridge, MA (US)

( * ) Notice: Subject to any disclaimer, the term of this patent is extended or adjusted under 35 U.S.C. 154(b) by 1229 days.

(21) Appl. No.: 13/694,575

(22) Filed: Dec. 13, 2012

(65) Prior Publication Data

US 2014/0165711 A1 Jun. 19, 2014

Related U.S. Application Data

(60) Provisional application No. 61/630,591, filed on Dec. 15, 2011.

(51) Int. Cl.
| G01N 1/02 | (2006.01) |
| B01L 3/00 | (2006.01) |
| G01N 1/00 | (2006.01) |
| A61B 10/00 | (2006.01) |

(52) U.S. Cl.
CPC ... *B01L 3/502715* (2013.01); *B01L 3/502723* (2013.01); *G01N 1/02* (2013.01); *A61B 10/007* (2013.01); *A61B 10/0051* (2013.01); *B01L 2200/027* (2013.01); *B01L 2200/0684* (2013.01); *B01L 2300/0838* (2013.01); *G01N 2001/002* (2013.01)

(58) Field of Classification Search
CPC .................................................. G01N 1/10
USPC ....................................................... 73/64.56
See application file for complete search history.

(56) References Cited

U.S. PATENT DOCUMENTS

| 8,101,431 | B2 * | 1/2012 | McDevitt et al. | 436/518 |
| 2006/0264779 | A1 * | 11/2006 | Kemp et al. | 600/583 |
| 2007/0009386 | A1 * | 1/2007 | Padmanabhan et al. | 422/68.1 |
| 2007/0166196 | A1 * | 7/2007 | Bardell et al. | 422/68.1 |
| 2007/0172388 | A1 * | 7/2007 | Padmanabhan et al. | 422/58 |

(Continued)

*Primary Examiner* — John Fitzgerald
*Assistant Examiner* — Rodney T Frank
(74) *Attorney, Agent, or Firm* — Danielson Legal LLC

(57) ABSTRACT

A system for collection and delivery of sub-milliliter liquid samples is described that provides a dramatic simplification for the measurement of clinical values. The system produces high dilutions of capillary size samples, such as bodily fluids or blood, by a factor of 1000 or more. Multiple assays can be conducted on a sample of 0.1 cc or less. A small lancet can create a drop of blood on a fingertip or other location, which can be collected into a self-priming capillary blood collector. The sample is then loaded into a consumable loader. Then a fluid, such as saline, is flowed into the consumable loader, and passes through the capillary collector, washing out the fluid. Downstream, the blood in the capillary is reliably diluted by mixing with appropriate reagents to allow analysis of selected blood properties. One or more individual bubbles can be inserted into the stream during loading. The capillary loading system can be used for one or several assays on a single blood sample. It can be very compact and lightweight and is suitable for use in remote environments, such as outer space, in which it is difficult to access diagnostic assays.

11 Claims, 13 Drawing Sheets

(56) References Cited

U.S. PATENT DOCUMENTS

2007/0224084 A1* 9/2007 Holmes et al. .............. 422/68.1
2010/0181199 A1* 7/2010 Sugiyama ................ C07K 1/26
                                                    204/601

* cited by examiner

OPEN — ONE SIDE LOADED FIRST — CLOSED

CAPILLARY MANIPULATION OF CLINICAL SAMPLES

This application claims the benefit of the priority of U.S. provisional application 61/630,591, which is incorporated herein by reference in its entirety.

BACKGROUND

Collecting blood samples and delivering aliquots of blood to one or several analytical instruments is a common procedure in medicine. Typically, a patient will have a needle placed in a vein, and multiple tubes containing specific reagents will be filled from that needle. Such a system is commonly encountered in doing a physical examination, or otherwise establishing the state of the patient. As an occasional practice, the drawing of ten to 100 milliliters of blood is normally not of concern. However, if done frequently, such volumes have a potential for lowering red cell density in the bloodstream.

A number of tests for specific conditions, which may need to be repeated frequently, begin by pricking a fingertip with a lancet. Blood flows from the site, and is collected in a capillary, or by collecting a droplet into a test tube or the like. Blood from the collected droplet is then placed in an assay system. This method is unlikely to alter patient blood parameters, but it is poorly suited for multiple tests. It can also be more painful than collecting blood from a vein.

In addition, in most medical situations, blood must itself be treated as a potentially infectious agent. Hence, minimization of potential exposure of personnel to blood is an additional goal. However, because staff time is expensive, the procedures must remain simple and fast even as exposure risk is reduced.

In light of these sometimes competing priorities, there is an ongoing need for simplification of sample handling when drawing blood. Similar considerations apply to clinical sampling of other bodily fluids.

SUMMARY OF THE INVENTION

An improved system is described for the introduction of clinical samples from a patient into an analytical system, and for the detection and analysis of properties of such samples. In the improved system, a capillary device and a consumable loader are used to transport a clinical sample from a source, such as a drop of blood, into an analytical device or system. In the capillary device, a capillary, which may be straight or curved, and which may contain sharp bends or branches, is loaded with a clinical sample to be analyzed. The capillary device is then connected to a device for loading consumables (a "consumable loader"), which in turn is connected to a fluid source upstream of the sample-containing capillary, and to a fluid pathway leading to an analysis system downstream of the consumable loader.

Flow of the upstream fluid source and the sample is initially separate except for diffusion at the interface. Bubbles may be placed at one or both ends of the sample in the capillary, for signaling the start or cessation of sample flow to the detection and analysis system, and for controlling the rate of sample mixing during flow through the system. The location of bubbles in the capillary sample has four options: bubble upstream, bubble downstream, bubbles on both sides, and no bubbles. (The upstream side is the direction of flow of liquid from a source leading into the capillary). In addition to being boundary markers, changing the location of the bubbles can give different sample dilution profiles during the analysis procedures, which in turn may be different for different sample types (CSF, blood, saliva, urine, etc.) or cell types (red blood cells, white blood cells, platelets, etc.).

After the sample is loaded, dilution of samples to suitable levels is accomplished by arranging for mixing of the sample with co-flowing diluent fluid as they flow together down a length of tubing, or other passage. In a preferred method, the sample and diluent are introduced into a tube in which they will initially flow side-by-side. The sample is then diluted further using two or more mixing zones selected from a variety of methods. In-line mixing of the sample with streams of one or more diluents or detection reagents is also possible. The diluted sample next passes through an analysis region including one or more detection modules, and the value of one or more parameters is measured.

Use of differing dilution fluids is available for handling a set of assays. The fluids may be used with a separate cassette, or may be loaded with additional blood from the sample or with blood from the same capillary. Such fluid may be separated by additional bubbles, or other markers.

Each assay is designed to be easily performed by a single person with minimal training. Because of its small size and simple fluidic pathway, the analytical system can be placed in a portable hand-held device, similar in size and weight to a portable telephone. Reporting from the device can be local or remote.

DETAILED DESCRIPTION OF THE INVENTION

Medical diagnosis and treatment have made many advances, but access to care is difficult in remote locations, and can be difficult in towns and cities, even in well-off countries. Many diagnostic assays require complex automatic equipment, which is typically located in a hospital or a specialized analytical laboratory. Alternatively, a few specific assays might be performed in the field by trained personnel. However, field assays can be difficult because of a lack of automated analysis equipment. Such problems are acute in outer space, or in a remote station, but are also visible in urban areas. One significant source of these problems is the need to maintain and operate complex equipment. While routine in a clinical laboratory, this is much more difficult in a remote site. Complex training is often needed but not feasible.

The present invention is directed to creating a simple, error-resistant, inexpensive system for collecting and analyzing samples for one assay or a panel of assays, using small, light weight analytical devices. The system is particularly directed to performing diagnostic routines in remote places, or in other locations where simple clinical analysis is not readily available.

Figure 1:
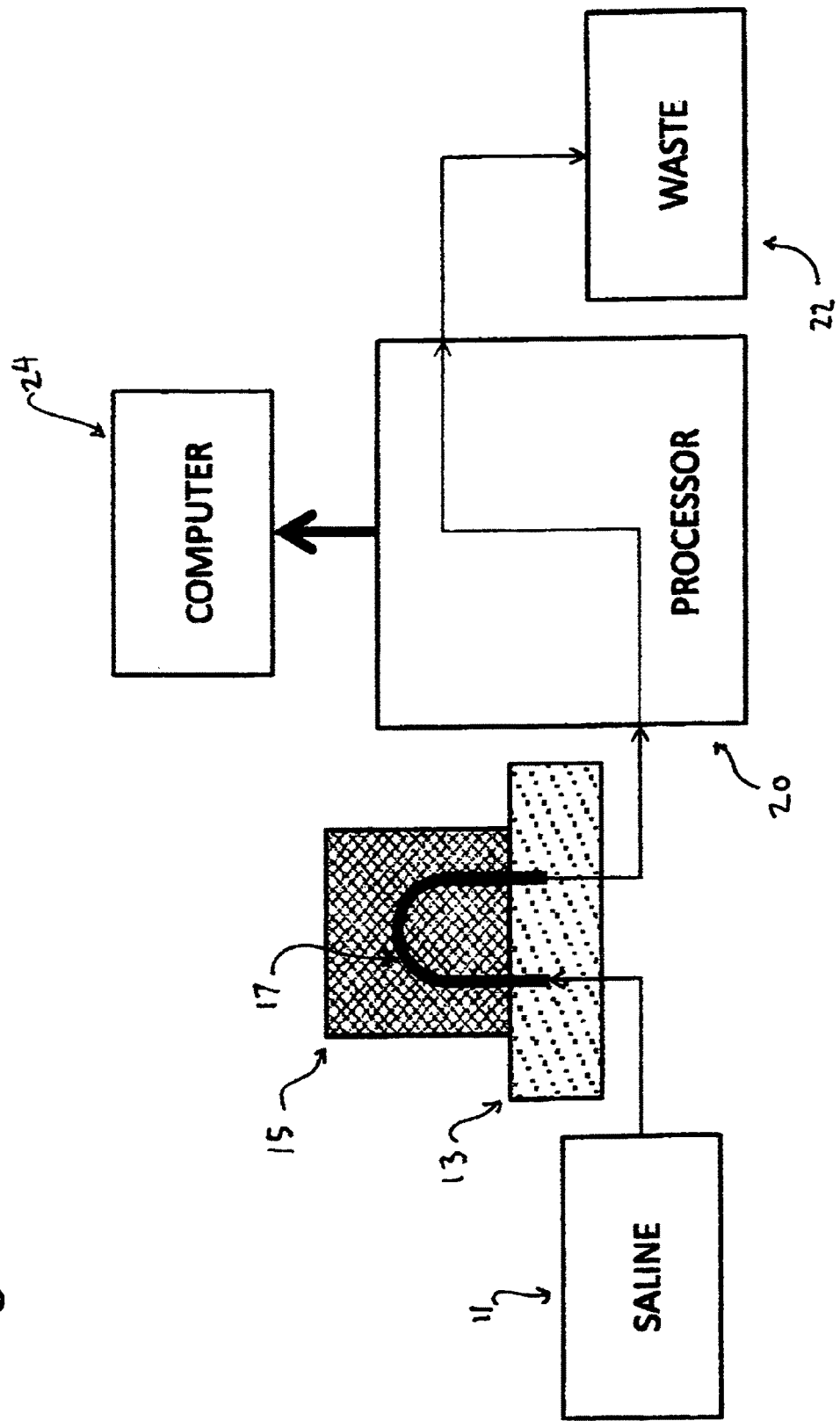
FIG. 1 shows a block diagram of the blood analysis system of the invention.

FIG. 1 shows a schematic flow diagram of the mixing and detection system. On the left, a reservoir of saline 11 supplies a consumable loader 13 with a flow of saline. The saline reservoir is typically pressurized to about 5 psi (ca. 0.7 atmosphere) when fluid is being moved. A capillary device 15 is used for transferring blood to the system, and includes a capillary 17 which is filled with collected blood. The capillary device 15 is connected to the consumable loader 13. The capillary device 15 carries a defined amount of sample in the capillary 17. Saline, optionally buffered, is a preferred diluent, but other solutions can also be used.

When the capillary device 15 is inserted into the consumable loader 13, the saline reservoir 11 is connected, via consumable loader 13, to the upstream end of the capillary device 15, and the downstream end of the capillary device 15 is connected to consumable loader 13, and then connects downstream to an analysis device and processor 20. A bubble may be inserted into the upstream and/or downstream ends of the capillary device 15, to help define the sample in the detection system, or to allow other forms of mixing. Optionally, depending on the design, O-rings or other fluid sealing elements may be provided in one or both of capillary device 15 and consumable loader 13.

If a sample is properly loaded, then dilutions of 1000 or more can be achieved in the tubing downstream of where the sample was loaded. The challenges of sample loading are consistent sample insertion, control of bubbles in the system, creating a good fluid seal, and the ability to load a defined volume of sample.

Once the capillary device 15 is in place in the system, flow from the saline reservoir 11 through the consumable loader 13 into the capillary 17 of the capillary device 15 begins. This flow washes through the capillary 17 and into a processor 20, displacing the sample downstream and beginning its dilution. The processor 20 may add additional reagents to the flowing sample, and has a detection system for one or more sample components of interest. After analysis, the sample is sent to a waste reservoir 22 for disposal. A computer 24, which may be integrated with the processor 20, reports and stores readings. The processor 20 is small, preferably hand-held, and has as major components an optical detection system, together with inputs for reagents, as described herein.

After the sample is cleared from capillary 17, the disposable capillary device 15 may be removed from the system, and may be discarded. Removal of capillary device 15 may interrupt the flow of saline through the system, either via low fluid pressure, or by a pressure sensor and a valve. This is desirable in some circumstances, to minimize use of consumables. Alternatively, the consumable loader 13 or a separate device (see below) may be placed to permit saline flushing when there is no sample in the system; or the state with no sample can be a fluid-conducting state, as shown below, and system flow control can be managed by valves or other controllable devices.

A second sample can be inserted into the system at any time, preferably after any background due to the first sample has cleared the detection system. Alternatively, there may be more than one location at which capillaries containing samples for analysis can be connected between a saline supply and the detection system. Likewise, there can be more than one detection location in the device, which may be downstream of a first detection location, or which could be in parallel with it if desired. The capillary device is preferably a disposable item, but could be cleaned on line, or in a separate cleaning circuit. In addition, a flow of pressurized saline or other fluid could be directed from reservoir 11 directly to the processor 20 for any needed purpose, including sample dilution as described below, and system flushing and cleaning. Likewise, a second reservoir with cleaning components (not illustrated) could be switched into the inlet to the consumable loader 13.

Figure 2:
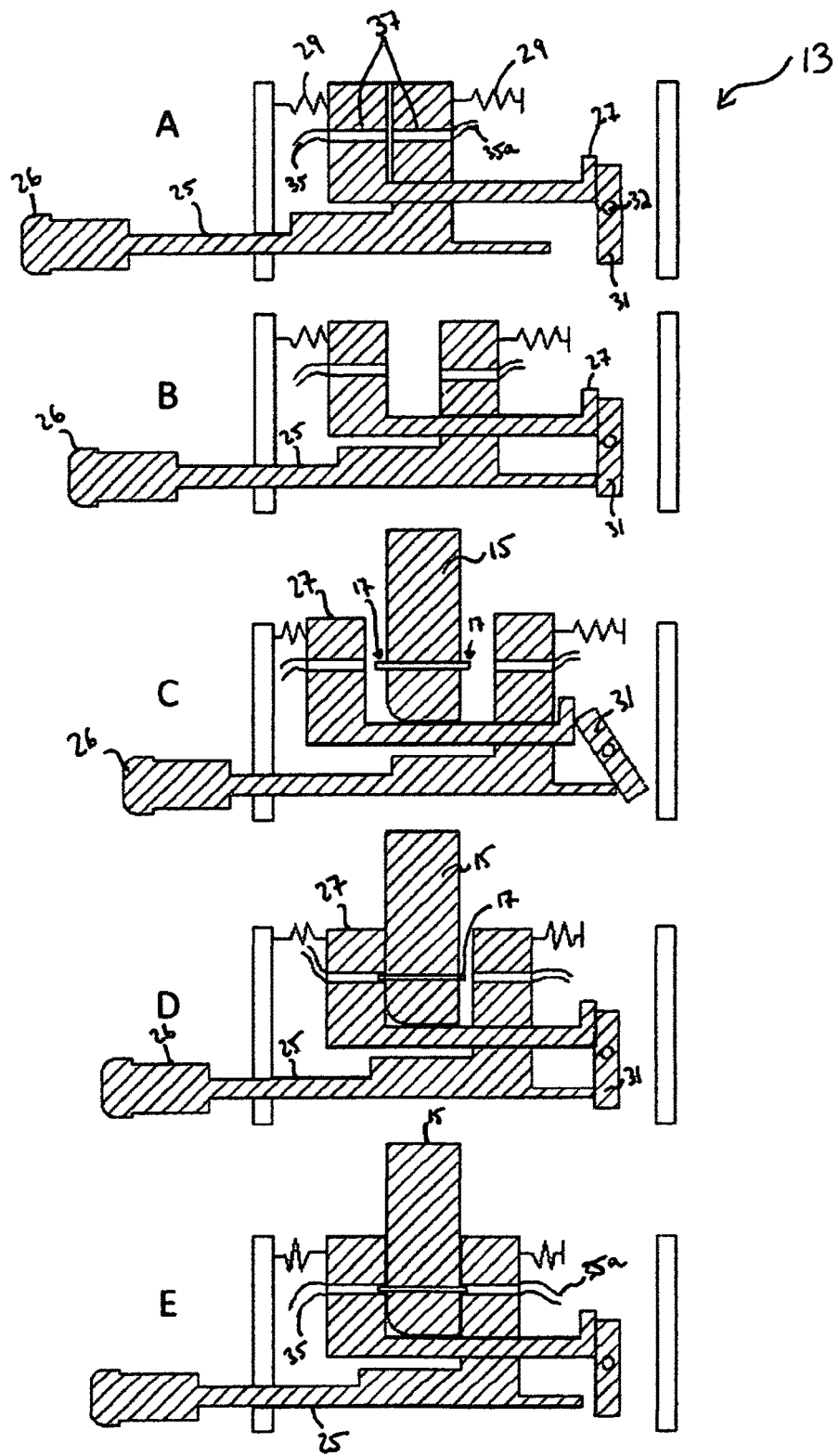
FIG. 2 shows the steps of an insertion of a capillary device carrying a sample into a consumable loader.

FIG. 2 shows cross-sectional detail of one version of a device and method for loading samples. In FIG. 2A, the consumable loader 13 is pictured without the capillary device 15 inserted. O-rings (not shown) can be used to create a seal between the driving side 25 and driven side 27 of the loader. Saline or other fluid can be driven though inlet/outlet tubing 35 to clean the device and/or prime the system. Priming acts to fill o-rings with a reservoir of saline. Forces from springs 29 act to restore the device to this position.

In FIG. 2B, pressing the button 26 forces the driving side 25 away from the driven side 27, breaking the seal and providing an opening for the insertion of the capillary device 15 (not shown). At this point, the driving side 25 is just about to contact the pivot 31.

In FIG. 2C, driving side 25 has contacted pivot 31, which then rotates about pin 32 and forces the driven side 27 to open away from the driving side 25, providing a large enough opening for the capillary device 15 to be inserted. Guide rails (not shown) may be used to ensure that the capillary device 15 is aligned properly relative to the consumable loader 13. In this embodiment, the sample is loaded into the side of the capillary 17 adjacent to the driven side 27.

In FIG. 2D, the user releases the button 26 once capillary device 15 is fully inserted. The pivot 31 couples the motion between the driving side 25 and driven side 27 so that both close equal amounts until the driven side 27 contacts the collection capillary 17. Saline pooled in the O-ring on the driven side 27 can create or enhance a fluid-fluid seal with the fluid in the capillary 17, and drives said fluid towards the other end of the capillary 17 so that no air remains.

In FIG. 2E, the driven side 27 can no longer move because it is in contact with the capillary device 15 which is fixed in place by guide rails (not shown). This leaves only the driving side 25 to move. The driving side 25 continues to close until it connects with the other side of the blood collection capillary 17. This enables flow through tubing 35 into capillary 17, containing sample to be analyzed, and flow out of the capillary 17 into the downstream side 35a of the tubing.

To remove the capillary device 15, pressing the button 26 will restore the loader 13 to the position in FIG. 2C, at which point the user can manually remove the capillary device 15. Releasing the button 26 will restore the consumable loader 13 to the position in FIG. 2A, the closed state, where it is ready for the next use.

The embodiment described above creates a no-bubble sample. To include a bubble on the leading or trailing edge, the sample should be loaded from the side adjacent to the driving side 25. Reversing the direction of flow determines which end of the sample contains a bubble.

Figure 3:
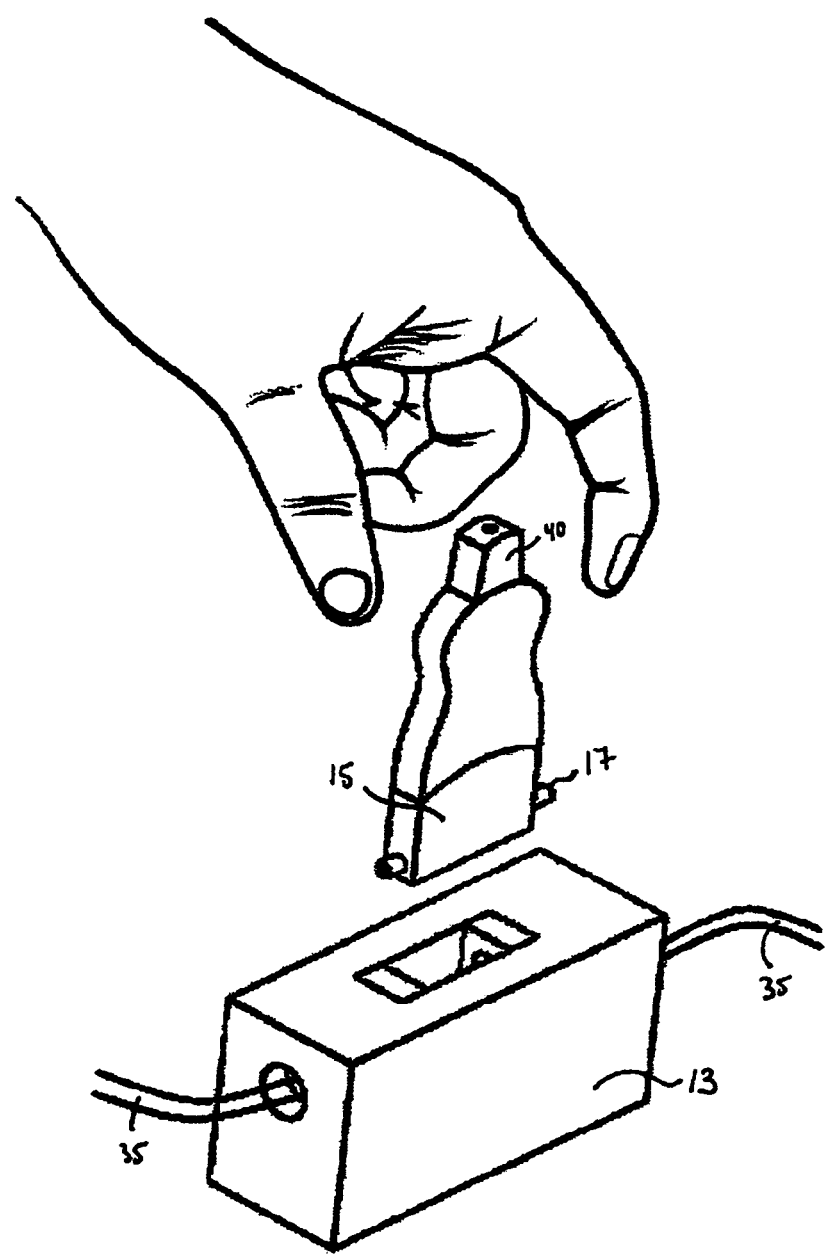
FIG. 3 shows a cartoon of the insertion of a capillary device, with associated lancet, into a consumable loader.

FIG. 3 shows a cartoon of the installation of a capillary device 15, with a capillary 17, into a consumable loader 13. The capillary 17 will connect to the fluid tubing 35, connecting upstream with the saline reservoir and downstream with the data processor. The cartoon format gives a sense of the scale of the devices of the invention, by contrast with the pictured hand. The capillary device 15, for example, which carries the capillary 17, is generally in the range of 10-60 mm in width and height, and 3 to 10 mm in thickness. The consumable loader 13 is depicted here as a stand-alone device, which is a common format in the development process, but it may be integrated with the processor 20 in the hand-held product format. The saline source 11, not shown here, is also efficiently integrated into a hand-held device, and integration is an option for the waste receptacle 22. In this cartoon, a single-use lancet 40 is also present, snap-connected to the capillary device 15 which is about to be loaded into (or is being removed from) consumable loader 13.

Figure 4:
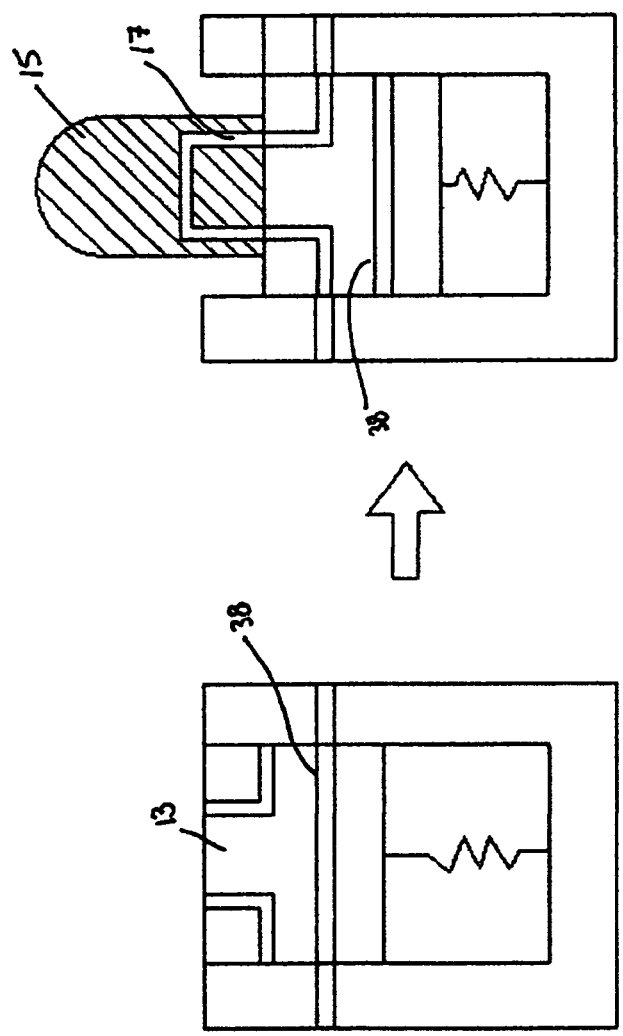
FIG. 4 shows a cross section of a capillary loader of the invention and its use.

In FIG. 4, a variation of the device of FIG. 1, separate fluid capillaries 38 can be provided, in the type of consumable loader 13 illustrated in Fig, 1, so that saline can be flushed through when a sample is not in the cell. (This is provided directly in the device of FIG. 2). The extra capillary 38 as illustrated could be in a spring-mounted version of consumable loader 13, so that capillary 38 would bridge the gap in consumable loader 13 as a default position, and thereby allow flow even when no capillary device 15 was placed in the fluid path (A). But when a capillary device 15 with a loaded capillary 17 is inserted, the inner part of the consumable loader 13 would slide away and not interfere with passage of fluid as shown in FIG. 1 or 3. This arrangement allows fluid flow into the device to be steady, so that a previous sample can reach the analysis section during the interval when another sample is being prepared for insertion into the system.

Figure 5:
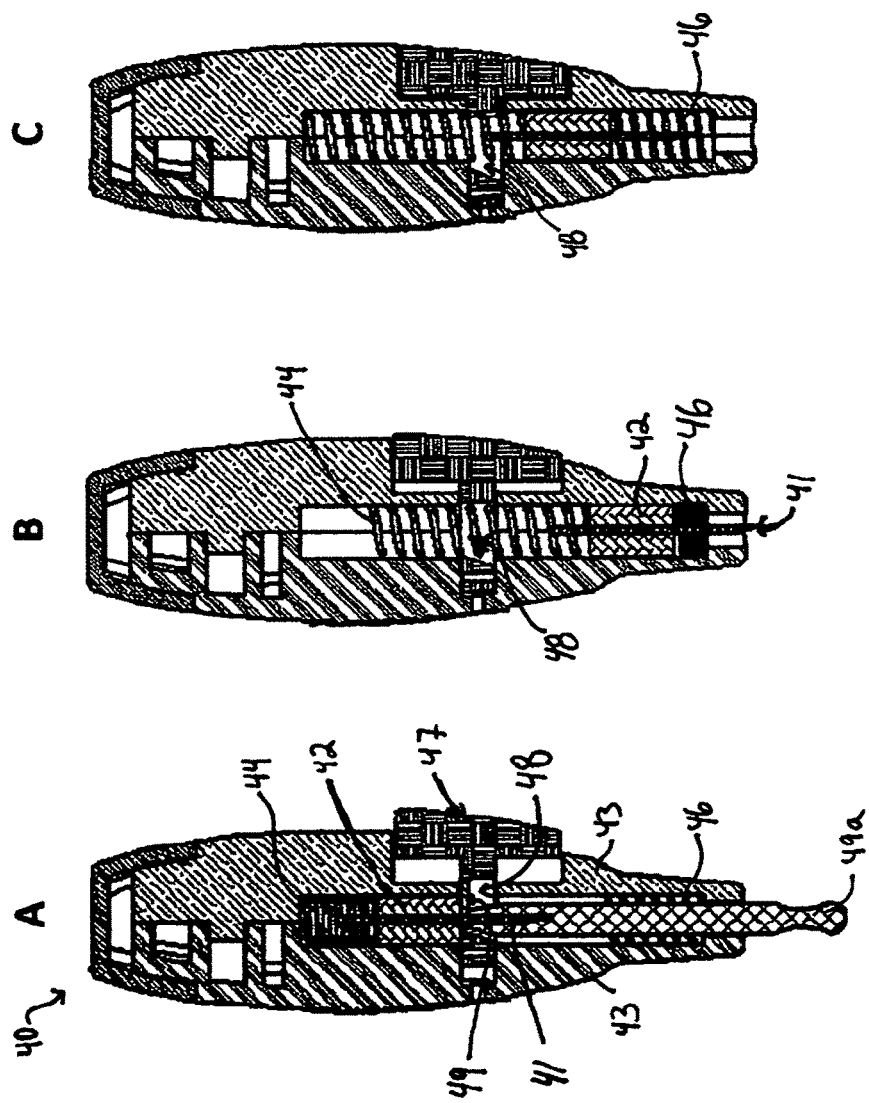
FIG. 5 shows a cycle of use of a lancet of the invention.

FIG. 5 shows a cross-section of a disposable lancet package 40 that can be used in the invention. In FIG. 5A, a cylindrical lancet 41 is embedded in a cylinder 42 which is placed between two casing halves 43 which create a tube around the cylinder 42. A stiff upper spring 44 is retained against the casing 43. Spring 44 opposes a more flexible return spring 46. The lancet cylinder 41 rests on the edge of a button 47, when the lancet is cocked. The button has a hole 48 in it, which is retained in a position which keeps the lancet cocked by a safety tab 49. When the cap 49a is removed the safety tab 49 is also withdrawn. When the button 47 is pressed, then the lancet is rapidly driven into the skin by the upper spring 44 (FIG. 5B). Next, the return spring 46 very quickly pushes the lancet back out of the skin (FIG. 5C), allowing a drop of blood to be formed on the surface of the skin. The lancet is safe because there is no way to re-cock it. The blood on the skin (not illustrated) is sampled by one or more capillary devices, such as the capillary device 15 of FIG. 1 or by other sampling means. The quick, automatic retraction of the lancet minimizes pain.

Figure 6:
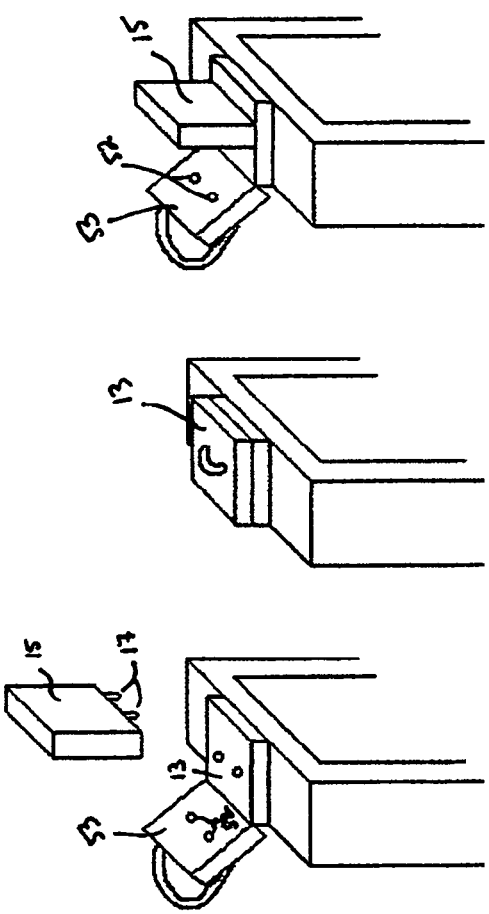
FIG. 6 shows a capillary device with capillary and a consumable loader.

FIG. 6 shows a use cycle of the consumable loader 13. In the first panel (left), any capillary device 15 (having capillary inlet and outlet 17) in the consumable loader 13 is removed, and the loader 13 is opened to allow cleaning. Then (center panel) the loader 13 is closed to allow priming of the loader and the rest of the fluid path with saline or other fluid. Fluid flow occurs, when the lid is closed, through a passage 52 in the lid 53 of the capillary loader 13, which can be seen in the left or right panels. Finally (right panel), a loaded capillary device 15 is inserted into the consumable loader, and the next test is ready to run.

Figure 7:
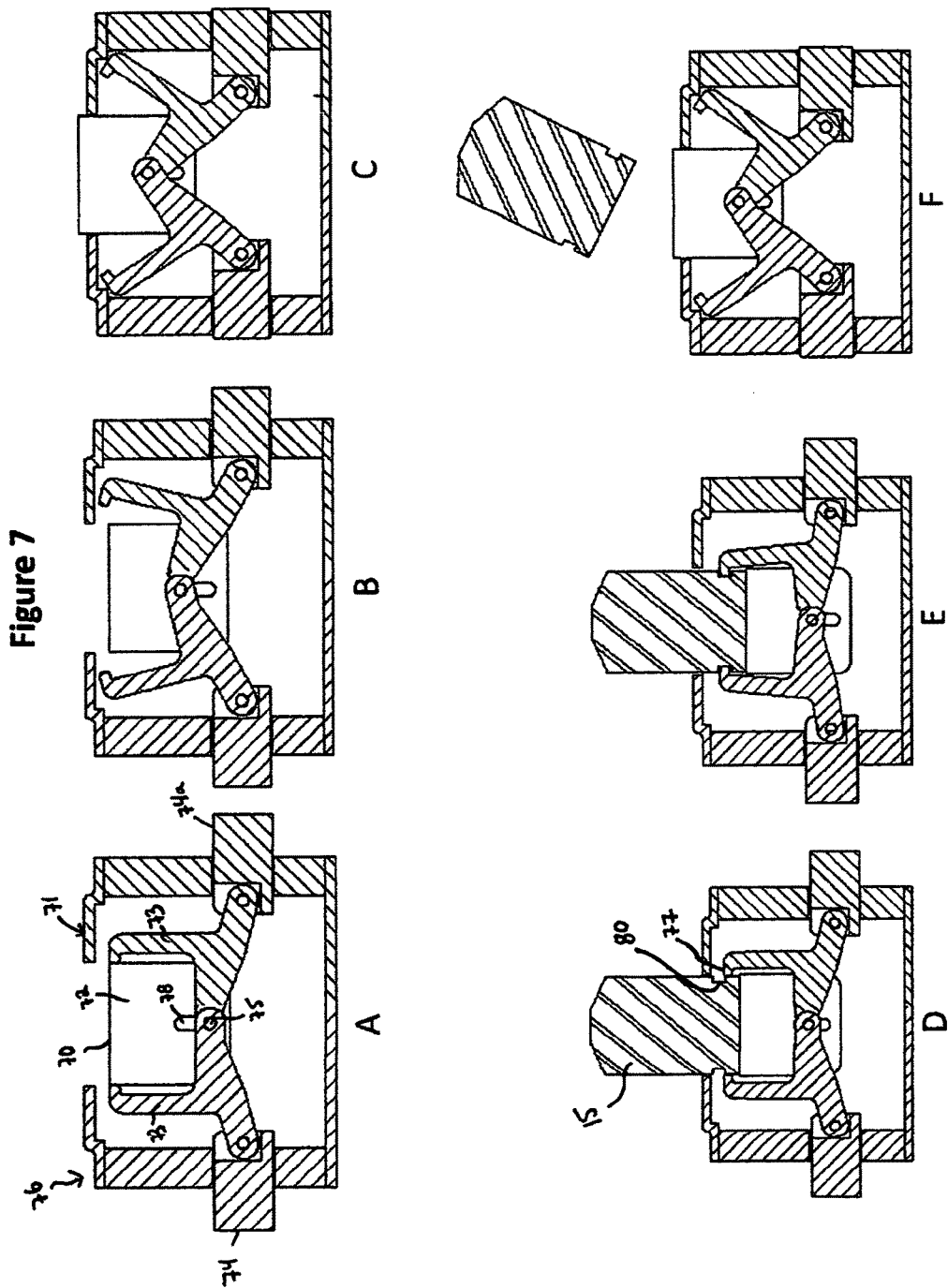
FIG. 7 shows a cycle of use of the consumable loader into which the capillary collector is inserted.

FIG. 7 shows a variation of FIG. 4 that is structured to prevent some types of user error. In the neutral position, shown in panel A, the linkages 73 rest against a moving insert 72. The loading surface 70 of the insert 72 sits below the surface 71 of the device. When the buttons 74/74a are pressed, as shown in panels A and B, the linkages 73 drive the insert driving pin 75 upwards in the insert travel slot 78. At first, the motion of the buttons 74 does not move the insert 72, as the pin 75 slides from the bottom to the top of slot 78 (panel B). Once the pin 75 reaches the top of the insert travel slot 78, as in panel B, the motion of the buttons 74 drives the insert 72 upwards until the guides on the moving insert 72 reach the top of the vertical guide track (not pictured). The device has reached this position in panel C. In this position, the loading surface 70 is fully exposed beyond the surface 71 of the device to allow for cleaning. Once cleaning is complete, release of buttons 74 drives the insert 72 back inside the device, returning to the position in panel A. When the consumable device 15 is inserted into the enclosure 76, it connects with the loading surface 70 on the insert 72 and drives the insert 72 downwards. The buttons 74 do not move, as the insert 72 moves relative to the insert driving pin 75. In panel D, when the capillary device 15 is fully inserted, the linkage lock feature 71 on the linkage 73 falls into a slot 80 on the capillary device 15, as seen in panel E. This action holds the capillary device 15 in place until buttons 74 are pressed (panel F), driving the insert 72 upwards and the capillary device 15 into a waste container (not pictured).

Figure 8:
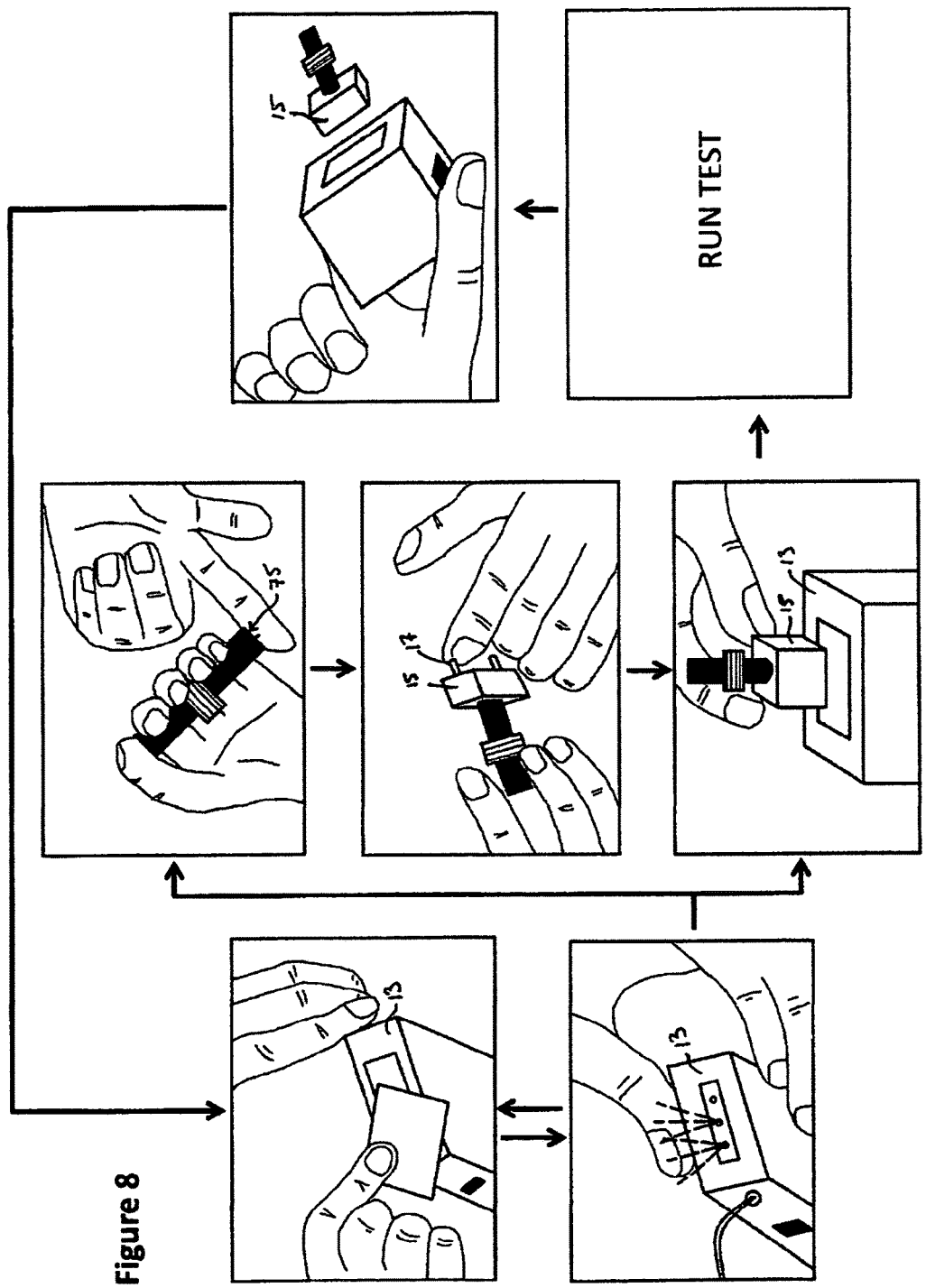
FIG. 8 shows the steps of testing a patient's blood with the system of the invention.

FIG. 8 shows the cycle of use of the devices of the invention. Panel A shows the cleaning of a consumable loader 13. In Panel B, the openings for sample flow through the consumable loader 13 are inspected and cleaned. From Panel B, in one branch of the work course, a sample is needed, leading to panel C, which shows a finger-tip pricking, in which a lancet 75 creates a blood sample. Blood is drawn into capillary 17 in Panel D. This blood sampling can either be done in real time, in the sequence shown, or the loaded capillary device 15 can be prepared previously. In Panel E, the loaded capillary device 15 is placed into consumable loader 13, and then tests are run (Panel F). Then the used capillary device 15 is discarded, and the consumable loader 13 returns to the state pictured in panel A for cleaning. Multiple capillary devices can be in use in a busy system. In a remote system or one seldom used, it may be efficient to discard capillary devices rather than recycle them.

Figure 9:
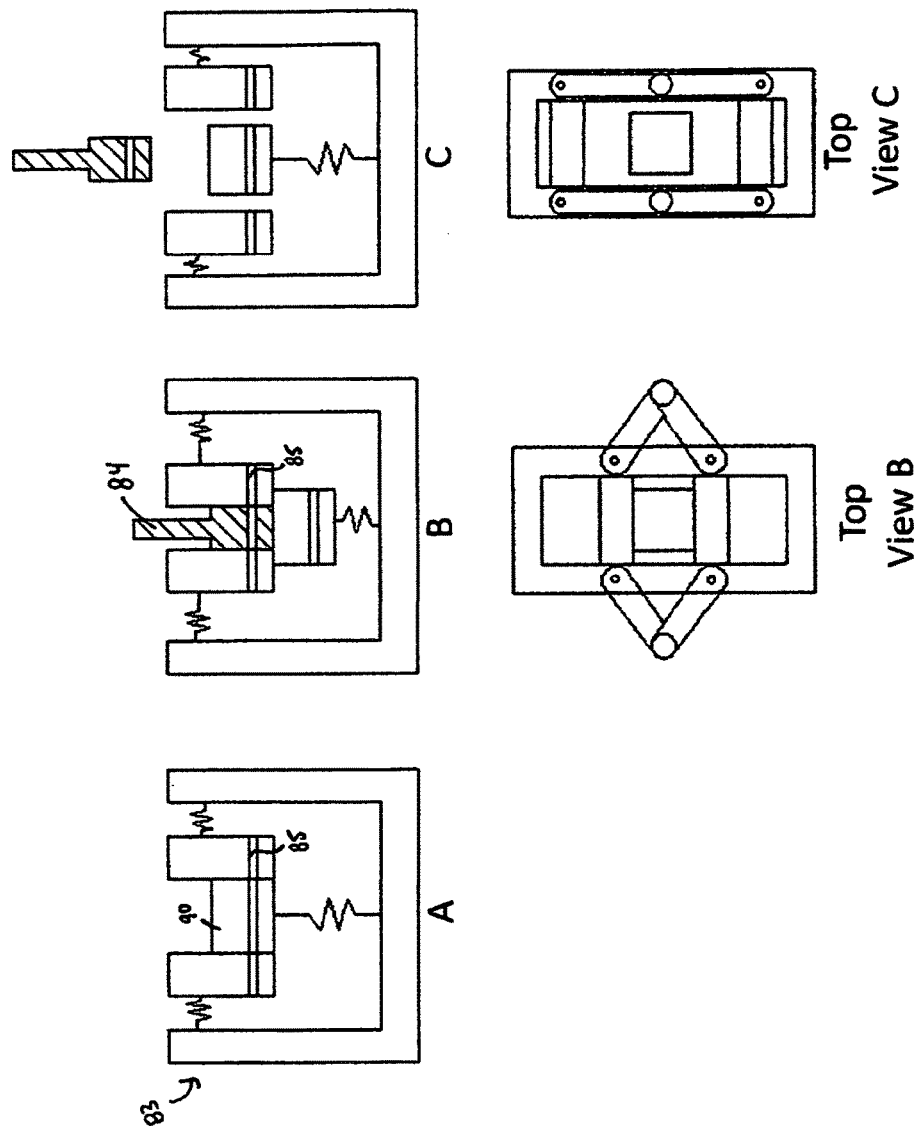
FIG. 9 shows a design in which the consumable loader is cleaned by a dummy consumable.

FIG. 9 shows a design in which the consumable loader 83 is cleaned by a dummy consumable 90. The dummy, which slides up and down in the consumable loader, is used to prime the consumable loader 83 as shown in panel A. Then, as shown in panel B, a capillary device 84, loaded with a sample by the procedures of FIG. 8 (above), is placed in the consumable loader and aligned so that flow through the consumable loader and the capillary device in channel 85 is possible. The consumable is released and discarded, as in panel C. The top view of panels B and C are shown to demonstrate a possible opening mechanism.

Figure 10:
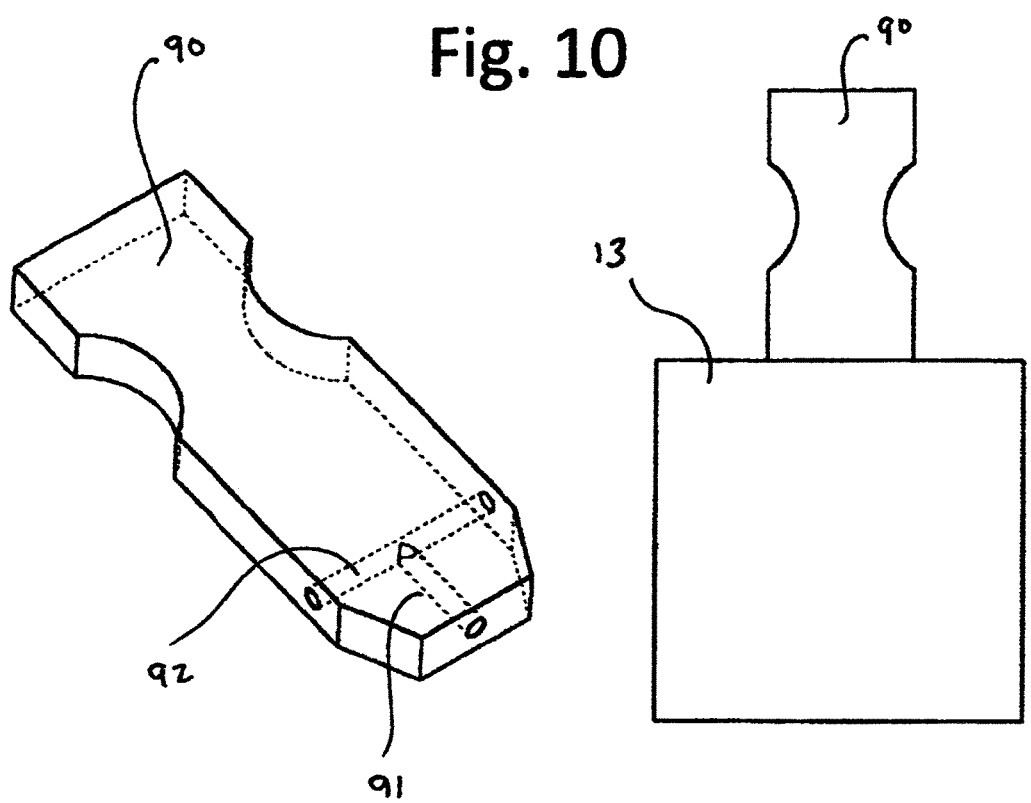
FIG. 10 shows a "T-shaped" capillary device for control of bubble placement.

FIG. 10 shows a T-shaped capillary device 90. The T-shaped consumable, functionally similar to the capillary device, is designed to precisely meter a sample of fluid into the capillary device in a way that gives control of the bubble location. The blood or bodily fluid sample is collected using the vertical portion of the T in the consumable. The T-shaped capillary fills from the bottom via capillary action, rising in capillary 91 and spreading horizontally in capillary 92. Upon insertion into the consumable loader 13, a pin in the loader (not shown) displaces a predetermined volume of fluid from the vertical portion of the T-loader. Fluid comes out the horizontal portions 62 of the T and fluid contact is made with receiving gaskets in the consumable loader to create a fluid seal (not illustrated). This approach allows a precise amount of fluid in the horizontal section of the T-consumable to be dispensed into the system. It also allows regulation so that bubbles can be placed where needed.

Figure 11:
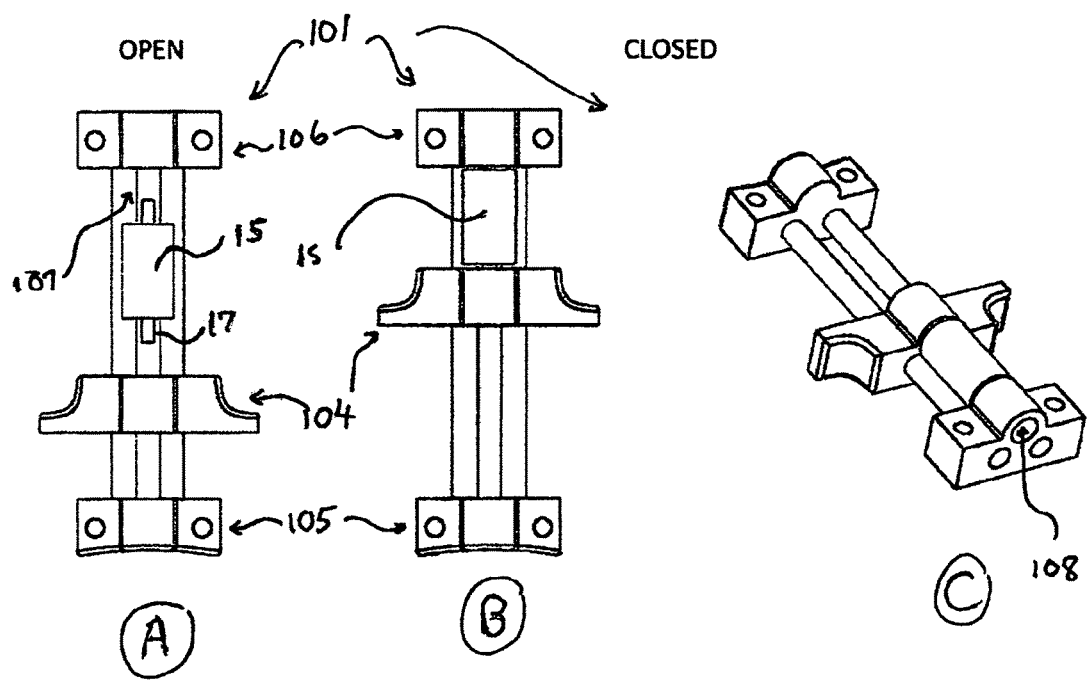
FIG. 11 shows a capillary device being inserted into a consumable loader.

FIG. 11 shows a different variety of consumable loader and capillary. In Panel A, the consumable loader 101 is open and accepts a capillary device 15 with capillary 17. The open state is made by finger action on grips 104 with respect to proximal end 105. The grips ride on rails 107. The capillary is preloaded with blood or other sample as previously described. In Panel B, the grips 104 are released and the capillary device 15 is captured between the distal structure 101 and the grips 104. Panel C shows a port 108 which is available to supply the contents of capillary device 15 to an analysis section.

Figure 12:
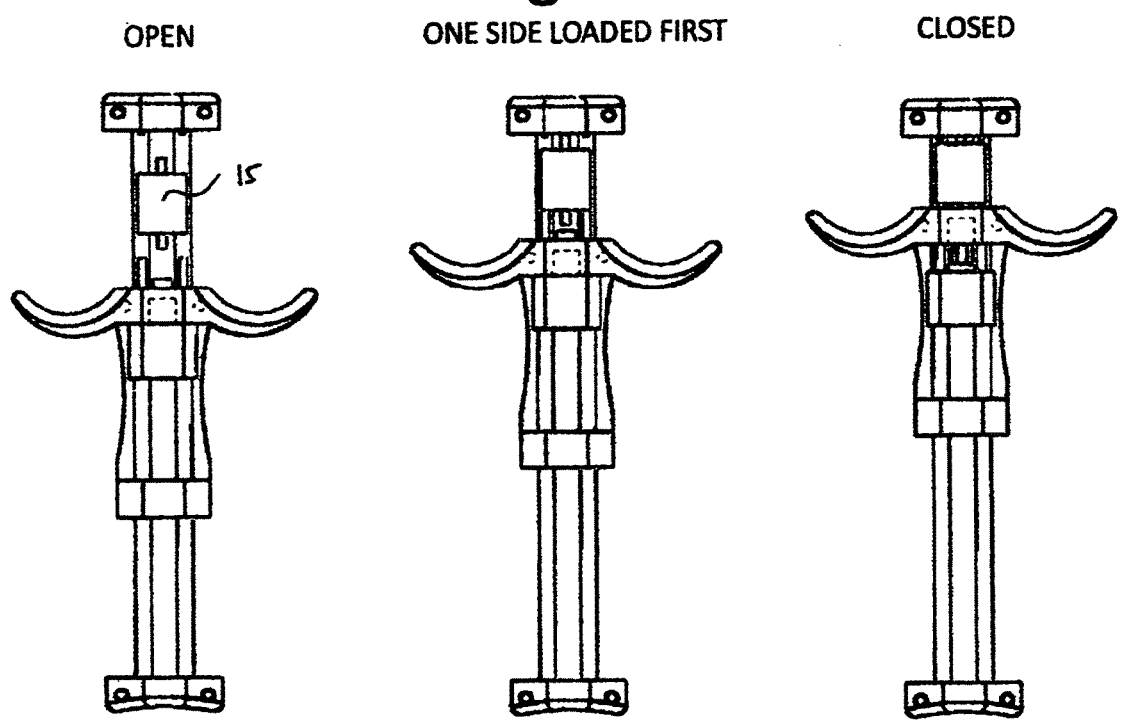
FIG. 12 shows a system for differentially loading bubbles into one end or the other of a capillary device.

FIG. 12 shows an in-line capillary loader, similar to that of FIG. 11. It has an asymmetric spring-loaded platform that allows the cylindrical capillary device 15 to be inserted into one O-ring before the other. This creates a possibility for asymmetric loading. By allowing one side of the consumable device to contact the O-ring first, precise control is gained over the manner in which bubbles are loaded. In particular, by contacting one side first, the fluid bulges out the back side of the capillary. This allows fluid seals to be made on both sides of the capillary device. This capillary device also has guiderails which position the cylindrical consumable precisely in-line with the rest of the system. Valving may be incorporated to ensure that fluid remains in the system during the loading process.

Figure 13:
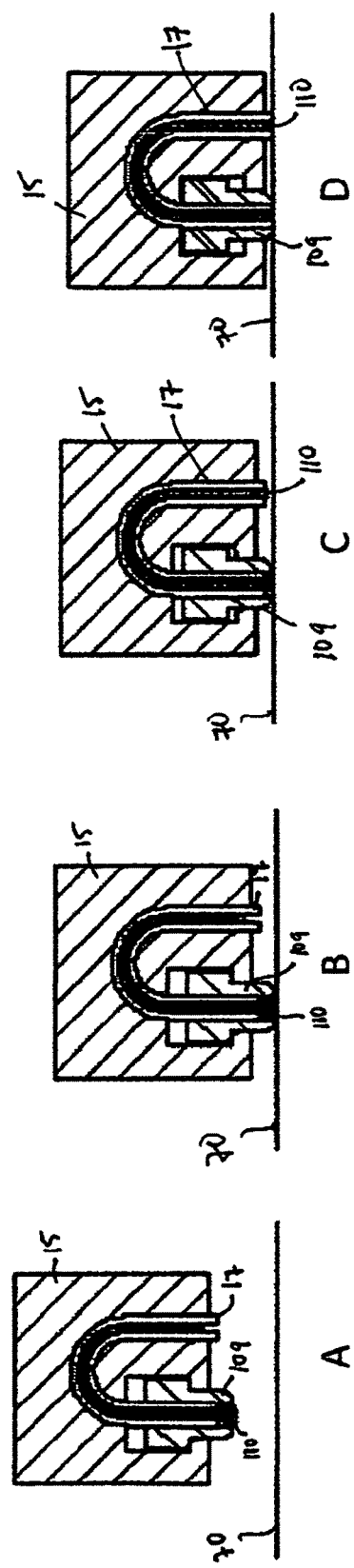
FIG. 13 shows a consumable design where a bubble elimination mechanism is integrated into the consumable.

FIG. 13 shows a consumable design that integrates bubble elimination independent of the consumable loader 13. In the starting position (FIG. 13A), the bubble eliminator 109 extends as far outside the consumable 15 as possible. The bubble eliminator 109 surrounds a small area of a larger diameter than the capillary 17, located between the end of the capillary and the end of the bubble eliminator 109. The sample 110 is drawn into the device filling the aforementioned area first. An area not filled with the sample 110 may exist on the far end of the capillary (right side in FIG. 13A). In FIG. 13B, the consumable 15 is pressed against the loading surface 79, creating a seal with the bubble eliminator 109. As the consumable device 15 is inserted further (FIG. 13C), the main body of the device moves towards the loading surface 70, but the bubble eliminator 109 remains stationary because it is already in contact with the loading surface 70. This action causes the bubble eliminator 109 to slide along the capillary 17. This motion reduces the volume available for sample collection and forces the sample 110 into the previously empty area. The sample 110 emerges from the far end of the capillary 17 before it comes in contact with the loading surface 79, thus ensuring no bubbles exist in the sample capillary 17. In FIG. 13D, the consumable 15 is fully inserted with no bubbles present.

Additional steps, not illustrated, can be added to the operation of the system. In particular, the processor 20 can have facilities for adding diluents or reagent streams to the entering fluid, and it will have detection means for measuring one or more properties of the sample. More than one detection system can be present in the processor.

Moreover, since the system of the invention is intended to be of use in remote areas and preferably on hand-held devices or equivalent, alternative modules for detection can be used. Because the volume of blood collectable from a single finger prick will typically be enough for many assays, the same blood sample can be used to fill many collection modules. Alternative detection reagents can be used, and the sample can be diluted to various extents. It is also possible to place one or more detection agents into the incoming saline stream if that is convenient. Moreover, different capillary lengths may be required for different assays.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference, where such incorporation is permitted. Nothing herein is to be construed as an admission that the invention is not entitled to antedate such disclosure by virtue of prior invention, where relevant. Those skilled in the art will recognize, or be able to ascertain using no more than routine experimentation, many equivalents to the specific embodiments of the invention described herein. Such equivalents are intended to be encompassed by the following claims.

The invention claimed is:

1. A system loading a fluid sample into a medical diagnostic instrument, the system comprising:
   a handheld capillary device configured to collecting the fluid sample into a T-shaped capillary within the handheld capillary device, wherein the T-shaped capillary has a vertical portion with a single first end and a horizontal portion with a second end and a third end; and
   a consumable loader configured to make a sealed connection to the first end, the second end, and the third end of the T-shaped capillary in a manner that allows the sample to be moved through the T-shaped capillary via flow;
   wherein the T-shaped capillary is configured to be filled with the fluid sample via the first end via capillary action, the fluid sample rising vertically within the vertical portion of the T-shaped capillary and subsequently spreading horizontally into the horizontal portion of the T-shaped capillary;
   the consumable loader further comprising a bubble eliminator located at one of the first, second, or third ends;
   wherein a dilution profile of the fluid sample is controlled, at least in part, by the bubble eliminator.

2. The system of claim 1, further comprising a detection system and a receiving means, the receiving means for collecting diluted sample and diluting fluid after it passes through said detection system.

3. The system of claim 1 wherein a one-use lancet, or an equivalent thereof, is provided for providing a liquid sample from a patient.

4. The system of claim 3, wherein the lancet has an integrated capillary for sample collection.

5. The system of claim 1, further comprising a collection device that collects 1-20 µL of sample.

6. The system of claim 5 wherein the dilution profile of the fluid sample is further controlled, at least in part, by the addition of one or more bubbles into the capillary device.

7. The system of claim 6 wherein the consumable loader includes an upstream port and a downstream port and said capillary device is differentially connected to one of the upstream and downstream ports of said consumable loader in order to control the effect of the addition of one or more bubbles.

8. The system of claim 7 wherein said T-shaped capillary, after being loaded with the fluid sample, has a bubble inserted at one or both ends.

9. The system of claim 1 wherein said sample is diluted in the range of about 100 fold to about 10,000 fold.

10. The system of claim 1 wherein said sample is diluted by the use of an inline mixing device.

11. The system according to claim 1, wherein a bubble is added or eliminated on at the start or end of said fluid sample at least during loading of said fluid sample.

* * * * *